(12) United States Patent
Foo

(10) Patent No.: US 7,635,789 B2
(45) Date of Patent: Dec. 22, 2009

(54) FLUOROALKYL ACID AMIDE SURFACTANTS

(75) Inventor: Thomas Foo, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 323 days.

(21) Appl. No.: 11/834,125

(22) Filed: Aug. 6, 2007

(65) Prior Publication Data

US 2009/0042997 A1  Feb. 12, 2009

(51) Int. Cl.
*C07C 235/06* (2006.01)
*C07C 233/05* (2006.01)
*C09G 1/06* (2006.01)
*C09K 13/00* (2006.01)
*A61K 47/16* (2006.01)
*C11D 1/00* (2006.01)

(52) U.S. Cl. .............. 564/159; 514/788; 510/467; 510/488; 510/505; 510/536; 252/79.1; 252/396; 55/290

(58) Field of Classification Search ............. 564/159; 514/788; 510/467, 488, 505, 536; 252/396, 252/79.1; 55/290

See application file for complete search history.

(56) References Cited

U.S. PATENT DOCUMENTS 3,621,059 A  11/1971  Costello et al.
5,035,841 A  7/1991  Costello et al.

FOREIGN PATENT DOCUMENTS

EP  0 144 844 B1  6/1985

*Primary Examiner*—Shailendra Kumar

(57) ABSTRACT

Compounds of formula (I) and formula (III):

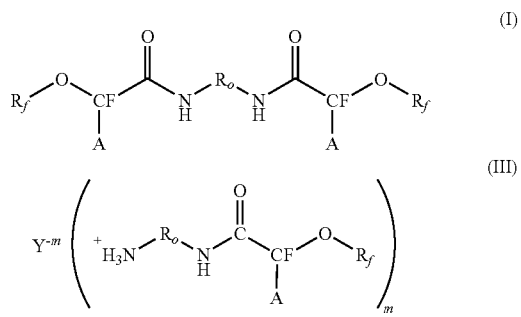

wherein
A is —F or —$CF_3$;
$R_f$ is independently $C_1$-$C_6$ perfluorinated linear or branched alkyl optionally interrupted by one or more oxygens; $R_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent; m is an integer of 1 to 3;
$Y^{-m}$ is an anionic radical selected from the group consisting of halide, $C_1$-$C_6$ carboxylate, carbonate, hydrocarbonate, sulfate, hydrosulfate, $C_1$-$C_6$ sulfonate, phosphate, hydrophosphate, and dihydrophosphate.

Further embodiments include methods of lowering surface tension of a medium comprising contacting the medium with a composition of formula (I), (III), or a mixture thereof.

16 Claims, No Drawings

FLUOROALKYL ACID AMIDE SURFACTANTS

FIELD OF INVENTION

The field of invention is related to the synthesis and use of fluorochemical surfactants.

BACKGROUND OF INVENTION

For surfactants and surface treatment agents with fluorochemical chains longer perfluoroalkyl chains contain a higher percentage of fluorine at a given concentration and provide better performance. However, fluorinated materials are more expensive. Reduction of the fluorine content with delivery of the same or higher performance is therefore desirable. Reducing the fluorine content would reduce the cost, but it is necessary to maintain product performance.

EP 0,144,844 B1 discloses a fluoroalkyl acid amide derived from acylation of a diamine with one equivalent of a fluorinated hydrocarbon acid or fluorinated oxyhydrocarbon acid radical as an intermediate in the preparation of a surfactant.

U.S. Pat. No. 5,035,841 discloses a bis-fluoroalkyl acid amide derived from acylation of a oxyalkylene diamine with a perfluorinated hydrocarbon acid radical.

U.S. Pat. No. 3,621,059 discloses amides derived from hexafluoropropylene oxide polymer acids and monoamine terminated polyalkylene oxide that function as surfactants and emulsifying agents.

It is desirable to improve surfactant or surface treating agent performance and to increase the fluorine efficiency, i.e., boost the efficiency or performance of the surfactants or treating agents so a lower proportion of the expensive fluorine component is required to achieve desired levels of performance, or to have better performance using the same level of fluorine. It is also desirable to have available surfactants based on a variety of fluorocarbon feed-stocks.

SUMMARY OF INVENTION

One aspect of the invention is a compound of formula (I):

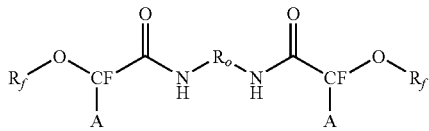

wherein

A is —F or —$CF_3$;

$R_f$ is independently $C_1$-$C_6$ perfluorinated linear or branched alkyl optionally interrupted by one or more oxygens;

$R_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent.

Another aspect of the invention is a compound of formula (III)

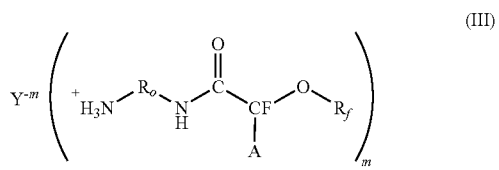

wherein m is an integer of 1 to 3

A is —F or —$CF_3$;

$R_f$ is independently $C_1$-$C_6$ perfluorinated linear or branched alkyl optionally interrupted by one or more oxygens;

$Y^{-m}$ is an anionic radical selected from the group consisting of halide, $C_1$-$C_6$ carboxylate, carbonate, hydrocarbonate, sulfate, hydrosulfate, $C_1$-$C_6$ sulfonate, phosphate, hydrophosphate, and dihydrophosphate.

Other embodiments of the invention are methods of lowering surface tension of a medium comprising contacting the medium with a composition comprising a compound of formulas (I) or (III).

DETAILED DESCRIPTION

All patents cited herein are hereby incorporated by reference.

All trademarks found herein are designated with capital letters.

One aspect of the invention is a compound comprising formula (I):

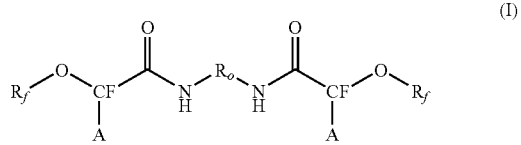

wherein

A is —F or —$CF_3$;

$R_f$ is independently $C_1$-$C_6$ perfluorinated linear or branched alkyl optionally interrupted by one or more oxygens;

$R_o$ is a linear or branched aliphatic group of about 10 to about 100 carbon atoms, interrupted by about 5 to about 50 ether oxygens, and more preferably about 20 to 40 carbon atoms interrupted by about 5 to about 20 ether oxygen, wherein the ratio of ether oxygen atoms to carbon atoms is about 1:2 to about 1:4; and more preferably, 1:2 to about 1:3; and wherein each carbon atom has at most one ether oxygen atom bonded to it, and covalent bonding between ether oxygen atoms is absent. In all embodiments herein, preferably $R_o$ has a molecular weight, when each valency is occupied by an —$NH_2$ group, of between about 200 to about 2200, and a solubility in water of 1 wt %, and more preferably 5 wt %, or higher. Preferably $R_o$ is a hydrophilic water-solvatable polyoxyalkylene radical of formula (IVa), (IVb), (IVc), or a mixture thereof:

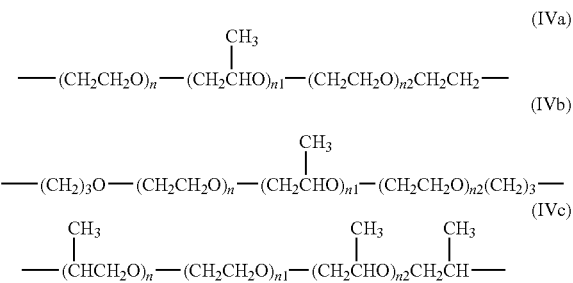

$$—(CH_2CH_2O)_n—(CH_2\overset{CH_3}{\underset{|}{C}HO})_{n1}—(CH_2CH_2O)_{n2}CH_2CH_2— \quad (IVa)$$

$$—(CH_2)_3O—(CH_2CH_2O)_n—(CH_2\overset{CH_3}{\underset{|}{C}HO})_{n1}—(CH_2CH_2O)_{n2}(CH_2)_3— \quad (IVb)$$

$$—(\overset{CH_3}{\underset{|}{C}HCH_2O})_n—(CH_2CH_2O)_{n1}—(CH_2\overset{CH_3}{\underset{|}{C}HO})_{n2}CH_2\overset{CH_3}{\underset{|}{C}H}— \quad (IVc)$$

wherein n is a positive integer, and n1 and n2 are each independently a positive integer or zero; said polyoxyalkylene radical having a weight average molecular weight up to about 2200.

Compounds of formula (I) are available by treatment of a diamine, $R_o(NH_2)_2$ with a fluoroalkyl acid halide, $X(O)CCF(A)OR_f$ according to scheme 1:

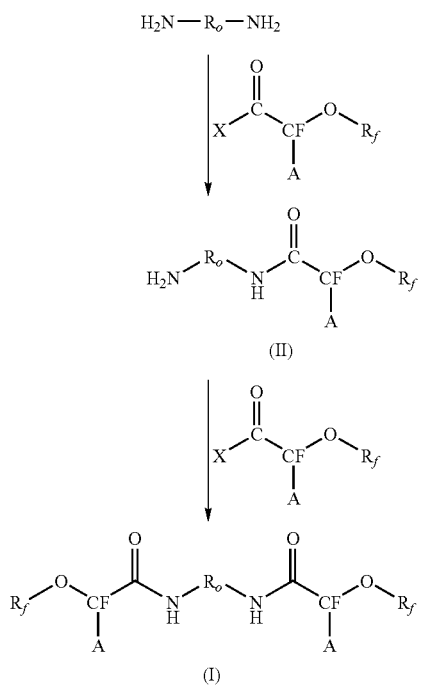

Scheme 1

Treatment of $R_o(NH_2)_2$ with 1 equivalent of the acid halide in the presence of a base, e.g. triethyl amine, provides the amino amide intermediate (II). The amino amide (II) composition available according to Scheme 1 is, in practice, a mixture of compounds including $R_o(NH_2)_2$ and the diamide (I). Further treatment with a second equivalent of the acid halide provides the bis-amide (I). The $R_o(NH_2)_2$ preferably are amine-terminated polyoxyalkylenes including amine terminated polyethylene glycol ethers ($NH_2$—PEG—$NH_2$), amine terminated polyethylene glycol-polypropylene glycol-polyethylene glycol triblock ethers ($NH_2$—PEG-PPG-PEG—$NH_2$) and amine terminated random copolymers of ethylene oxide and propylene oxide. They are available by synthesis by treatment of the corresponding hydroxy terminated polymers with thionyl chloride and ammonia. Commercial examples of these materials are JEFFAMINE® polyoxyalkyleneamines ED-600 (XTJ-500, MW 600), ED-900 (XTJ-501, MW 900), ED-2003 (XTJ-502, MW 2000), and HK-511 (MW 220), available from Huntsman Chemical (The Woodlands, Tex.)

Preferably the amine-terminated polyoxyalkylenes have about 5 to about 20 repeat units, and more preferably about 10 to 20 repeat units. Amine-terminated polyoxyalkylenes for preparing compositions of the invention have a water solubility of 1 wt %, and more preferably a water solubility of 5 wt %, or higher. These materials typically are predominately polyethylene glycol (PEG) based and are therefore more hydrophilic than polypropylene glycol (PPG) based materials.

Fluorinated carboxylic acid halides useful in the synthesis of compositions of formula (I) and (II) include the hexafluoropropylene oxide dimer (compound D1), available from E.I. du Pont de Nemours and Company, Wilmington, Del.; and the telomer acid fluoride, compound D2 wherein s=1 to 4. The telomer acid fluorides including compound D2, wherein s=1, are available by synthesis as disclosed in British Pat. No. 1,097,679 and Afonso, et al, Phys. Chem. Chem. Phys., 2000, 2 1393-1399.

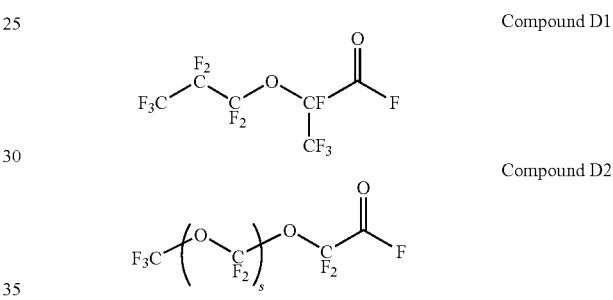

Other useful compounds are the branched telomer acid fluorides of formula D3, wherein v=1 to 3, that are available by synthesis as described in U.S. Pat. No. 3,692,843.

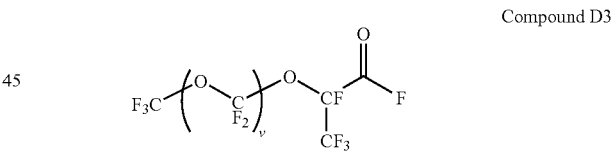

The term "optionally interrupted by one or more oxygens" in reference to the $R_f$ radical means that the carbon chain comprising the $R_f$ radical can be interrupted by one or more oxygen atoms, so long as the oxygens are bonded only to carbon; that is, there are no oxygen-oxygen bonds. Compounds of formula (I) wherein $R_f$ is interrupted by one or more oxygen atoms are typically derived from acyl fluorides such as D2 and D3 above.

In all embodiments herein preferably $R_f$ is a $C_1$-$C_3$ perfluorinated linear hydrocarbon.

Another embodiment is a compound of formula (III) wherein $Y^{-m}$ is an anionic radical selected from the group consisting of halide, $C_1$-$C_6$ carboxylate, carbonate, hydrocarbonate, sulfate, hydrosulfate, $C_1$-$C_6$ sulfonate, phosphate, hydrophosphate, and dihydrophosphate; m is an integer of 1 to 3; and $R_o$, $R_f$ and A are as disclosed above. Treatment of the amino amide intermediate (II) with a Bronsted acid provides compounds of formula (III) as shown in Scheme 2:

Scheme 2

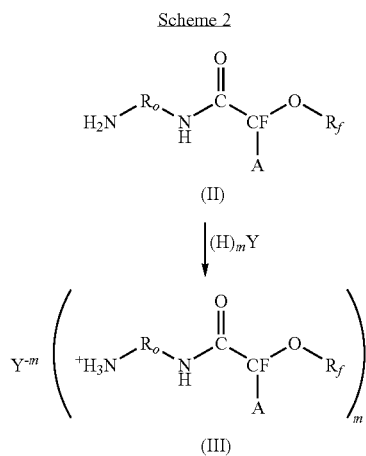

A Bronsted acid is defined in terms of proton transfer equilibria. A Bronsted acid possesses at least one acid hydrogen atom capable of being donated to a base, and for this application, the Bronsted acid has a $pK_a$ of about 7.0 or less in water. Bronsted acids $(H)_mY$, wherein m is an integer of 1 to 3, useful in forming compounds of formula (III) include those selected from the group consisting of: hydrogen halides including hydrogen fluoride, hydrogen chloride, hydrogen bromide and hydrogen iodide; hydrogen sulfates including sulfuric acid, and monohydrogen sulfate; hydrogen phosphates including phosphoric acid, dihydrogen phosphate, monohydrogen phosphate; dihydrogen carbonate; alkyl acids including formic, acetic and propionic acids; alkyl sulfonic acids including methyl sulfonic acid, ethyl sulfonic acid.

Some embodiments include compounds of formula (III), wherein m=1, and $Y^{-m}$ is $X^-$, represented by formula (IIIa) in Scheme 3, wherein $R_o$, A and $R_f$ are as defined above; and $X^-$ is fluoride, chloride or bromide; and more preferably, wherein $X^-$ is fluoride. Compounds of formula (IIIa) are alternatively available by treatment of $R_o(NH_2)_2$ with 1 equivalent of the acid halide in the absence of any base as shown in Scheme 3:

Scheme 3

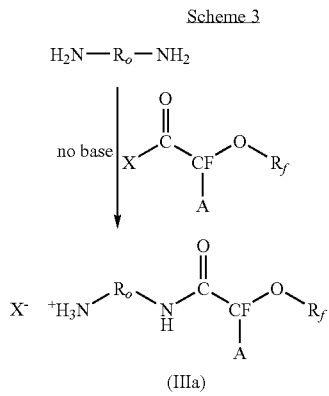

The present invention further comprises a method of lowering surface tension of a medium comprising contacting the medium with a composition of formula (I) as defined above. Another embodiment comprises a method of lowering surface tension of a medium comprising contacting the medium with a composition of formula (III) as defined above. Any of a wide variety of media are suitable for use in these methods. Typically the medium is a liquid. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition. The composition is typically simply blended with or added to the medium.

The present invention further comprises a method of providing leveling to a coated substrate comprising adding to the coating base prior to deposition on the substrate, a composition comprising one or more compounds of formula (I) as described above.

The present invention further comprises a method of providing leveling to a coated substrate comprising adding to the coating base prior to deposition on the substrate, a composition comprising one or more compounds of formula (III) as described above.

Embodiments for $R_o$ and $R_f$, disclosed above for compounds of formula (I), are also applicable to the embodiments of compounds of formula (III) and the methods for providing leveling using compounds of formula (I) and (III), respectively.

Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

The term "alkyd coating" as used herein means a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

The term "urethane coating" as used hereinafter means a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

The term "unsaturated polyester coating" as used hereinafter means a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

The term "water-dispersed coatings" as used herein means coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

The term "dried coating" as used herein means the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

The compounds of formula (I) and (III) are useful as surfactants and leveling agents in aqueous solutions and emulsions. It is further useful to alter the surface properties of such media. For example, surface properties such as surface tension, and leveling are altered by adding a composition of the present invention to the media. The compositions of the present invention have enhanced fluorine efficiency compared to current commercial products in wetting and leveling tests.

Methods and Materials

Test Method 1

The surface tension measurements of the surfactants were measured in fresh MILLIPORE filtered water using the Wilhelmy plate method on a Sigma70 tensiometer (KSV Instruments Inc., Monroe, Conn.) used in accordance with the manufacturers' manuals. MILLIPORE filters are available from Millipore Corporation, Billerica, Mass. The samples were initially prepared at a concentration equal to the highest concentration to be measured and diluted in the following series: 0.1, 0.01, 0.003, 0.001, 0.0003, and 0.0001% by weight. Each concentration was automatically measured 5 times and the average and standard deviation determined by the instrument. All vessels were cleaned and rinsed thoroughly first with tap water, then deionized water, then triple rinsed with MILLIPORE filtered water. After the measurements beakers were dried, and they were optionally cleaned in a plasma-cleaning oven for 5 minutes.

Test Method 2

Surface tension measurements of the surfactants measured in RHOPLEX 3829 floor polish, supplied by Rohm & Haas, Spring House, Pa., were made using the Wilhelmy plate method on a Kruess tensiometer (K11 version 2.501, Matthews, N.C.) used in accordance with the manufacturers' manuals. A 0.5 wt % surfactant solution in RHOPLEX 3829 floor polish was first prepared, and then diluted to the various concentrations using additional RHOPLEX 3829 floor polish.

Test Method 3—Wetting and Leveling Test

To test the performance of the samples in their wetting and leveling ability, the samples were added to a floor polish (RHOPLEX 3829 was used to prepare the final testing formulation) and applied to half of a stripped 12 inch×12 inch (30.36 cm×30.36 cm) vinyl tile. A 1% by weight solution of the surfactant to be tested was prepared by dilution in deionized water. Following the manufacturer protocols, a 100 g portion of the RHOPLEX 3829 formulation was prepared, followed by addition of 0.75 g of the 1% by weight surfactant solution, to provide a test floor polish.

The test floor polish was applied to a tile by placing 3 mL portion of the test polish in the center of the tile, and spreading from top to bottom using an applicator, and finally placing a large "X" across the tile, using the applicator. The tile was allowed to dry for 25-30 min and a total of 5 coats were applied. After each coat, the tile was rated on a 1 to 5 scale (1 being the worst, 5 the best) on the surfactant's ability to promote wetting and leveling of the polish on the tile surface. The rating was determined based on comparison of a tile treated with the floor polish that contained no added surfactant according to the following scale:

Subjective Tile Rating Scale

1 Uneven surface coverage of the film, significant streaking and surface defects 2 Visible streaking and surface defects, withdrawal of the film from the edges of the tile 3 Numerous surface defects and streaks are evident but, generally, film coats entire tile surface 4 Minor surface imperfections or streaking 5 No visible surface defects or streaks.

Perfluoro-2-methyl-3-oxahexanoyl fluoride (HFPO dimer) was obtained from E.I. du Pont de Nemours and Company (Wilmington, Del.).

JEFFAMINE ED-2003 from Huntsman Chemical, also known as XTJ-502, is an polyether diamine based predominately on a polyethylene glycol backbone having about 39 PEG repeat units to about 6 propylene glycol repeat units and an approximate molecular weight of about 2000. JEFFAMINE ED-600 from Huntsman Chemical, also known as XTJ-500, is an polyether diamine based predominately on a polyethylene glycol backbone having about 9 PEG repeat units to about 3.6 propylene glycol repeat units and an approximate molecular weight of about 600. JEFFAMINE ED-900 from Huntsman Chemical, also known as XTJ-501, is an polyether diamine based predominately on a polyethylene glycol backbone having about 12.5 PEG repeat units to about 6 propylene glycol repeat units and an approximate molecular weight of about 900.

Example 1

Examples 1-2 illustrate the synthesis of compounds of formula (III).

JEFFAMINE ED-600 (4.0 g, 6.7 mmol) was dissolved in diethylether (21 g) and cooled to −10° C. in a glovebox freezer. To the stirred mixture was slowly added HFPO dimer (2.2 g, 6.6 mmol) at room temperature (RT). The mixture was allowed to stir overnight at RT, and the solvent was then removed under vacuum to provide the product as a waxy residue. Maldi-MS, $^{19}$F NMR and IR analyses indicated the formation of the desired amide product mixture. Elemental analysis of the amide product mixture indicated about 20.9 wt % F. A portion of the reaction product mixture (2.25 g) was dissolved in isopropanol (20.03 g) to provide a 10.1 wt % stock solution for surface tension measurements and end-use testing.

Example 2

JEFFAMINE ED-900 (4.24 g, 4.7 mmol) was dissolved in THF (23 g) and cooled to −10° C. in a glovebox freezer. To the stirred mixture was slowly added HFPO dimer (1.56 g, 4.7 mmol) at RT. The mixture was allowed to stir overnight at RT, and the solvent was then removed under vacuum to provide the reaction product as a waxy residue. Maldi-MS, $^{19}$F NMR and IR analyses indicated the formation of the desired amide product mixture. Elemental analysis of the amide product mixture indicated about 16.3 wt % F. A portion of the reaction product mixture (2.13 g) was dissolved in isopropanol (19.27 g) to provide a 10.0 wt % stock solution for surface tension measurements and end-use testing.

Comparative Example A

Comparative Example A consisted of a fluoroalkyl ethoxylate surfactant (commercially available from E. I. du Pont de Nemours and Company, Wilmington, Del.), containing a mixture of perfluoroalkyl homologues ranging from 2 to 16 carbon atoms, predominantly 6, 8 and 10 carbon atoms. The surface tension was measured in MILLIPORE filtered water using Test Method 1.

The surface tension of solutions of Examples 1, 2 and Comparative Example A in MILLIPORE filtered water was measured using Test Method 1. The results are listed in Table 1. The results indicate that Examples 1 and 2 do provide a significant decrease in surface tension, but are not as effective as the commercial surfactant of Comparative Example A. However, Examples 1 and 2 have about one-half to about ⅓ the fluorine content of the Comparative Example A.

TABLE 1

Surface Tension in Deionized Water

| Concentration wt % active | Surface Tension, mN/m Example | | | | | |
|---|---|---|---|---|---|---|
| | Ex 1 | | Ex 2 | | Comparative A | |
| | wt % F (×10³) | | wt % F (×10³) | | wt % F (×10³) | |
| 0 | | | >70 | | | |
| 0.001 | 35.5 | 0.21 | 54.5 | 0.16 | 30.7 | 0.46 |
| 0.01 | 23.5 | 2.1 | 28.2 | 1.6 | 19.6 | 4.6 |
| 0.1 | 22.5 | 21 | 22.3 | 16 | 19.0 | 46 |
| 0.5 | 21.9 | 105 | 22.7 | 80 | 18.4 | 230 |

The surface tension of solutions of Examples 1, 2 and Comparative Example A in a commercial Rohm & Haas floor polish (RHOPLEX 3829) was measured using Test Method 2. The results are listed in Table 2. The results indicate that Examples 1 and 2 provide a decrease in surface tension in the RHOPLEX floor polish, and are almost as effective as the commercial surfactant of Comparative Example A; at about one-half to one-third the fluorine content.

TABLE 2

Surface Tension in RHOPLEX 3829 Floor Polish (N-29-1)

| Concentration wt % active | Surface Tension, mN/m Example | | | | | |
|---|---|---|---|---|---|---|
| | Ex 1 | | Ex 2 | | Comparative A | |
| | wt % F (×10³) | | wt % F (×10³) | | wt % F (×10³) | |
| 0 | | | 30.4 | | | |
| 0.001 | 28.9 | 0.21 | 26.9 | 0.16 | 24.7 | 0.46 |
| 0.01 | 27.7 | 2.1 | 27.4 | 1.6 | 26.0 | 4.6 |
| 0.1 | 24.2 | 21 | 24.3 | 16 | 22.4 | 46 |
| 0.5 | 21.9 | 105 | 22.0 | 80 | 17.8 | 230 |

Examples 1, 2 and Comparative Example A were tested for performance in their wetting and leveling ability in commercial floor polish according to Test Method 3. The results are listed in Table 3.

TABLE 3

Ratings for Wetting and Leveling Test

| Coating No. | Rating Example | | | | Dry Time, minutes |
|---|---|---|---|---|---|
| | Control | Comparative A | Ex 1 | Ex 2 | |
| 1 | 2 | 3 | 3 | 3 | 30 |
| 2 | 1 | 4 | 4 | 4 | 30 |
| 3 | 1 | 4 | 4 | 4 | 30 |
| 4 | 1 | 4 | 4 | 4 | 30 |
| 5 | 1 | 4 | 4 | 4.5 | 30 |
| Average | 1.2 | 3.8 | 3.8 | 3.9 | |

The data in Table 3 indicate that Examples 1 and 2 performance in the Wetting and Leveling test are comparable to the Comparative Example A; using ⅓ to ½ the fluorine content of the commercial surfactant.

Example 3

Examples 3-5 illustrate the synthesis of compounds of formula (I).

The Huntsman Jeffamine mixture ED-600 (6.0 g, 10.0 mmole, MW 600) and triethylamine (2.42 g, 24 mmole) were dissolved in diethylether (40 mL) and cooled in a glovebox freezer to about −10° C. A magnetic stirbar was added to this pre-cooled solution. To the stirred mixture was slowly added HFPO dimer (6.64 g, 20.0 mmole) at RT. The resulting reaction mixture was allowed to stir overnight at RT. The reaction solvent and excess triethyl amine were removed to provide the desired fluorinated diamide and the Et$_3$N—HF salt as a waxy residue. Maldi-MS and $^{19}$F NMR analyses indicated the formation of the desired diamide product mixture. Elemental analysis of the diamide product and Et$_3$N—HF salt mixture indicated about 32.7 wt % F. A portion of the product (1.20 g) was dissolved in isopropanol (8.80 g) to provide an approximately 10 wt % stock solution of the diamide product (12 wt % total including the Et$_3$N—HF salt) for surface tension measurements and end-use testing.

Example 4

The Huntsman Jeffamine mixture ED-900 (9.0 g, 10.0 mmole, MW 900) and triethylamine (2.42 g, 24 mmole) were dissolved in diethylether (40 mL) and cooled in a glovebox freezer to about −10° C. A magnetic stirbar was added to this pre-cooled solution. To the stirred mixture was slowly added HFPO dimer (6.64 g, 20.0 mmole) at RT. The resulting reaction mixture was allowed to stir overnight at RT. The reaction solvent and excess triethyl amine were removed to provide the desired fluorinated diamide and the Et$_3$N—HF salt as a waxy residue. Maldi-MS and $^{19}$F NMR analyses indicated the formation of the desired diamide. Elemental analysis of the diamide product and Et$_3$N—HF salt mixture indicated about 25.7 wt % F. A portion of the product (1.16 g) was dissolved in isopropanol (8.84 g) to provide an approximately 10 wt % stock solution of the diamide product (11.6 wt % total including the Et$_3$N—HF salt) for surface tension measurements and end-use testing.

Example 5

The Huntsman Jeffamine mixture ED-2003 (10.0 g, 5.0 mmole, MW 2000) and triethylamine (1.21 g, 12 mmole) were dissolved in tetrahydrofuran (40 mL) and cooled in a glovebox freezer to about −10° C. A magnetic stirbar was added to this pre-cooled solution. To the stirred mixture was slowly added HFPO dimer (3.32 g, 10.0 mmole) at RT. The resulting reaction mixture was allowed to stir overnight at RT. The reaction solvent and excess Et$_3$N were removed to provide the desired fluorinated diamide and the Et$_3$N—HF salt as a waxy residue. Maldi-MS and $^{19}$F NMR analyses indicated the formation of the desired diamide product. Elemental analysis of the diamide product and Et$_3$N—HF salt mixture indicated about 15.6 wt % F. A portion of the diamide product (1.09 g) was dissolved in isopropanol (8.91 g) to provide an approximately 10 wt % stock solution of the diamide product (10.9 wt % total including the Et$_3$N—HF salt) for surface tension measurements and end-use testing.

The surface tension of solutions of Examples 3, 4, 5, Comparative Example A, and the Et$_3$N—HF salt in MILLIPORE filtered water was measured using Test Method 1. The results are listed in Table 4.

TABLE 4

| | Surface Tension in Deionized Water | | | | | | | |
|---|---|---|---|---|---|---|---|---|
| | Surface Tension, mN/m | | | | | | | |
| | Example | | | | | | | |
| | Ex 3 | | Ex 4 | | Ex 5 | | Comparative A | |
| Conc. wt % | | wt % F (×10$^3$) | | wt % F (×10$^3$) | | wt % F (×10$^3$) | | wt % F (×10$^3$) | Et$_3$NHF |
| 0 | | | | | >70 | | | | |
| 0.0001 | 36.5 | 0.039 | 36.2 | 0.030 | 39.5 | 0.017 | 68.1 | 0.046 | >70 |
| 0.001 | 22.7 | 0.39 | 26.3 | 0.30 | 31.2 | 0.17 | 30.5 | 0.46 | |
| 0.01 | 22.5 | 3.9 | 22.1 | 3.0 | 23.0 | 1.7 | 20.7 | 4.6 | |

The surface tension data show no effect of the Et$_3$N—HF salt on the surface tension of water. Furthermore, the compounds of the present invention act to reduce the surface tension of water at fluorine levels that are significantly lower than that of the commercial fluorosurfactant.

What is claimed is:
1. A compound of formula (I):

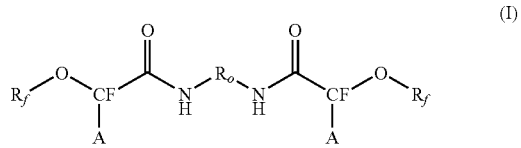

wherein
A is —F or —CF$_3$;
R$_f$ is independently C$_1$-C$_6$ perfluorinated linear or branched alkyl optionally interrupted by one or more oxygens;
R$_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent.

2. The compound of claim 1 wherein $R_o$ has a molecular weight of about 200 to about 2200 when each valency is occupied by an —$NH_2$ group and a solubility in water of 1 wt % or higher.

3. The compound of claim 1 wherein $R_o$ is a hydrophilic water-solvatable polyoxyalkylene radical of formula (IVa), (IVb), (IVc), or a mixture thereof:

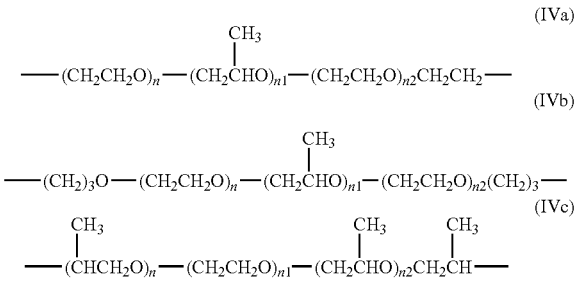

wherein n is a positive integer, and n1 and n2 are each independently a positive integer or zero; said polyoxyalkylene radical having a weight average molecular weight up to about 2200.

4. The compound of claim 1 wherein $R_f$ is a $C_1$-$C_3$ perfluorinated linear hydrocarbon.

5. A compound of formula (III)

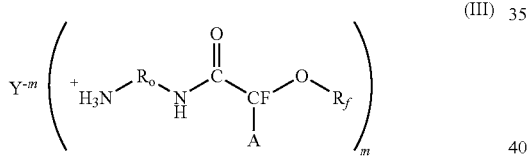

wherein m is an integer of 1 to 3

A is —F or —$CF_3$;

$R_f$ is independently $C_1$-$C_6$ perfluorinated linear or branched alkyl optionally interrupted by one or more oxygens;

$Y^{-m}$ is an anionic radical selected from the group consisting of halide, $C_1$-$C_6$ carboxylate, carbonate, hydrocarbonate, sulfate, hydrosulfate, $C_1$-$C_6$ sulfonate, phosphate, hydrophosphate, and dihydrophosphate;

$R_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent.

6. The compound of claim 5 wherein $R_o$ has a molecular weight, when each valency is occupied by an —$NH_2$ group, of between about 200 to about 2200, and a solubility in water of 1 wt % or higher.

7. The compound of claim 5 wherein $R_o$ is a hydrophilic water-solvatable polyoxyalkylene radical of formula (IVa), (IVb), (IVc), or a mixture thereof:

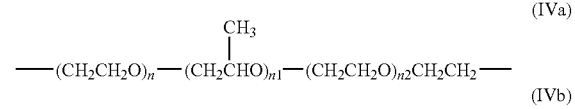

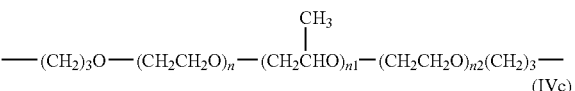

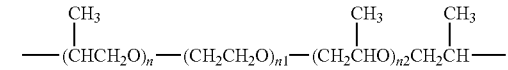

wherein n is a positive integer, and n1 and n2 are each independently a positive integer or zero; said polyoxyalkylene radical having a weight average molecular weight up to about 2200.

8. The compound of claim 5 wherein $R_f$ is a $C_1$-$C_3$ perfluorinated linear hydrocarbon.

9. A method of lowering surface tension of a medium comprising contacting the medium with a composition comprising a compound of formula (I)

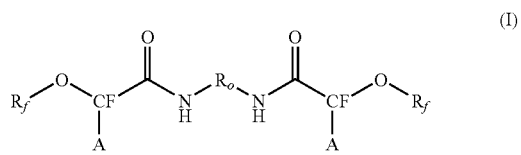

wherein

A is —F or —$CF_3$;

$R_f$ is independently $C_1$-$C_6$ perfluorinated linear or branched alkyl optionally interrupted by one or more oxygens;

$R_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent.

10. The method of claim 9 wherein $R_o$ has a molecular weight, when each valency is occupied by an —$NH_2$ group, of between about 200 to about 2200, and a solubility in water of 1 wt % or higher; and $R_f$ is a $C_1$-$C_3$ perfluorinated linear hydrocarbon.

11. The method of claim 9 wherein $R_o$ is a hydrophilic water-solvatable polyoxyalkylene radical of formula (IVa), (IVb), (IVc), or a mixture thereof:

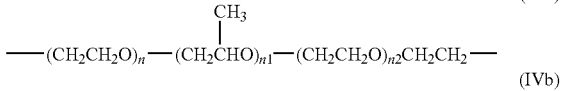

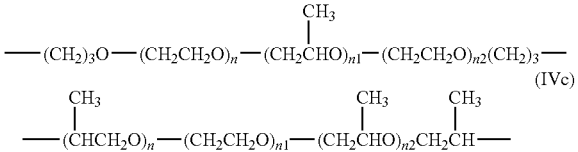

wherein n is a positive integer, and n1 and n2 are each independently a positive integer or zero; said polyoxyalkylene radical having a weight average molecular weight up to about 2200.

12. The method of claim 9 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

13. A method of lowering surface tension of a medium comprising contacting the medium with a composition comprising a compound of formula (III)

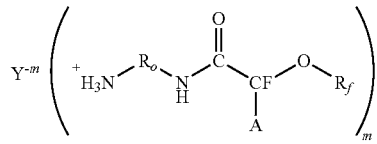

(III)

wherein

A is —F or —$CF_3$;

$Y^{-m}$ is an anionic radical selected from the group consisting of halide, $C_1$-$C_6$ carboxylate, carbonate, hydrocarbonate, sulfate, hydrosulfate, $C_1$-$C_6$ sulfonate, phosphate, hydrophosphate, and dihydrophosphate;

$R_f$ is independently $C_1$-$C_6$ perfluorinated linear or branched alkyl optionally interrupted by one or more oxygens;

$R_o$ is a linear or branched aliphatic group of about 10 to about 100 carbon atoms, interrupted by about 5 to about 50 ether oxygens, wherein the ratio of ether oxygen to carbon atoms is about 1:2 to about 1:3; and wherein each carbon atom has at most one ether oxygen atom bonded to it, and covalent bonding between ether oxygen atoms is absent.

14. The method of claim 13 wherein $R_o$ has a molecular weight, when each valency is occupied by an —$NH_2$ group, of between about 200 to about 2200, and a solubility in water of 1 wt % or higher; and $R_f$ is a $C_1$-$C_3$ perfluorinated linear hydrocarbon.

15. The method of claim 13 wherein $R_o$ is a hydrophilic water-solvatable polyoxyalkylene radical of formula (IVa), (IVb), (IVc), or a mixture thereof:

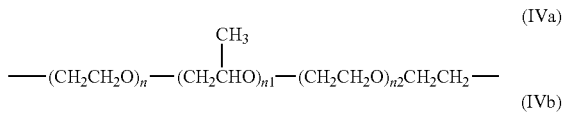

(IVa)

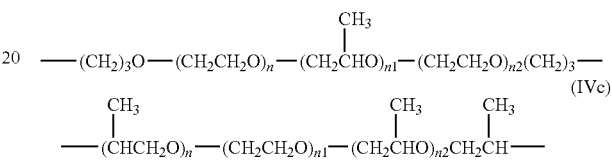

(IVb)

(IVc)

wherein n is a positive integer, and n1 and n2 are each independently a positive integer or zero; said polyoxyalkylene radical having a weight average molecular weight up to about 2200.

16. The method of claim 13 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

* * * * *